United States Patent [19]

Young

[11] 4,362,630
[45] Dec. 7, 1982

[54] SIDE STREAM MONITORING

[75] Inventor: Dale A. Young, Basking Ridge, N.J.

[73] Assignee: Exxon Research and Engineering Co., Florham Park, N.J.

[21] Appl. No.: 224,597

[22] Filed: Jan. 12, 1981

Related U.S. Application Data

[63] Continuation of Ser. No. 58,301, Jul. 17, 1979, abandoned, which is a continuation of Ser. No. 818,154, Jul. 22, 1977, abandoned.

[51] Int. Cl.$^3$ .............................................. B01D 35/14
[52] U.S. Cl. .................................. 210/745; 210/799; 210/85
[58] Field of Search ................. 210/85, 86, 96.1, 101, 210/94, 95, 98, 263, 502, 745, 799; 73/421 B, 422 R; 137/88, 89, 104, 559; 55/279, 274

[56] References Cited

U.S. PATENT DOCUMENTS

| | | | |
|---|---|---|---|
| 626,760 | 6/1889 | Kohn | 210/181 |
| 1,042,203 | 10/1912 | Dahl | 210/340 |
| 1,187,046 | 6/1916 | DeLamarter | 210/341 |
| 1,515,080 | 11/1924 | Strachan et al. | 210/338 |
| 1,696,735 | 12/1928 | Scoville | 210/95 |
| 1,909,655 | 5/1933 | Buquor | 210/85 |
| 1,943,811 | 1/1934 | Child et al. | 210/181 |
| 2,168,125 | 8/1939 | Hurn | 210/131 |
| 2,302,552 | 11/1942 | Johnson | 252/10 |
| 2,369,857 | 2/1943 | Russell et al. | 210/502 |
| 2,679,320 | 5/1954 | Walton | 210/168 |
| 2,843,077 | 7/1958 | Leefer | 116/117 |
| 2,951,156 | 8/1960 | Miller | 250/43.5 |
| 3,077,989 | 2/1963 | Larkin | 210/98 |
| 3,412,786 | 11/1968 | Taylor | 165/5 |
| 3,572,507 | 3/1971 | Juskevic | 210/97 |
| 3,658,180 | 4/1972 | Prosser | 210/96 |
| 3,765,226 | 10/1973 | Strickland et al. | 73/53 |

Primary Examiner—John Adee
Attorney, Agent, or Firm—Eugene Zagarella, Jr.

[57] ABSTRACT

A side stream monitoring device for a main unit such as a vessel, which effectively has the same geometrical and dynamic characteristics as those corresponding components in the vessel for enabling the side stream monitor to provide a ready indication and continuous monitor of the performance characteristics and quality of the corresponding components in the vessel, upon removal and testing or examination of the device. The apparatus and method for monitoring have particular utility in connection with clay filters or filter separators which are used for the removal of contaminants from, e.g. jet fuels. In each case a bypass side stream is disposed between the inlet and outlet lines of the filter or filter separator and located within the bypass line is a device which effectively is a reduced scale replica of a portion of the main unit which corresponds to the critical operating components thereof. For the clay filter a duplication of flow velocities and residence times of the fuel through a predetermined section of one of the main filter elements is reproduced. In the case of the filter separator, the side stream device comprises sections which are comprised of identical elements used in the main unit, including metal screens, fiber sheets, fiberglass screens, etc., except that each component of the side stream monitor is of a reduced size such that the ratio of the cross-sectional area to the liquid flow is the same as that which exists in the main unit for that particular component.

2 Claims, 6 Drawing Figures

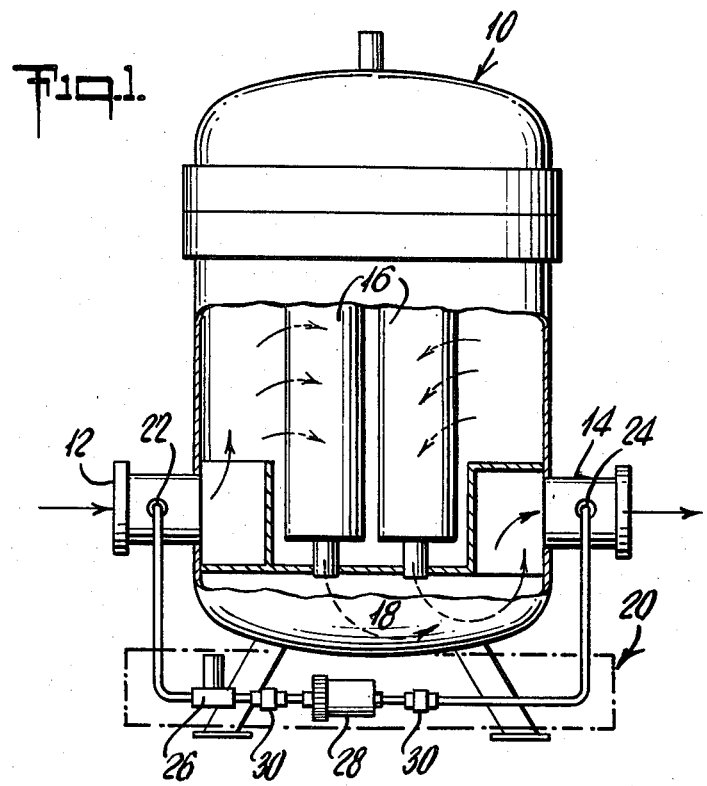
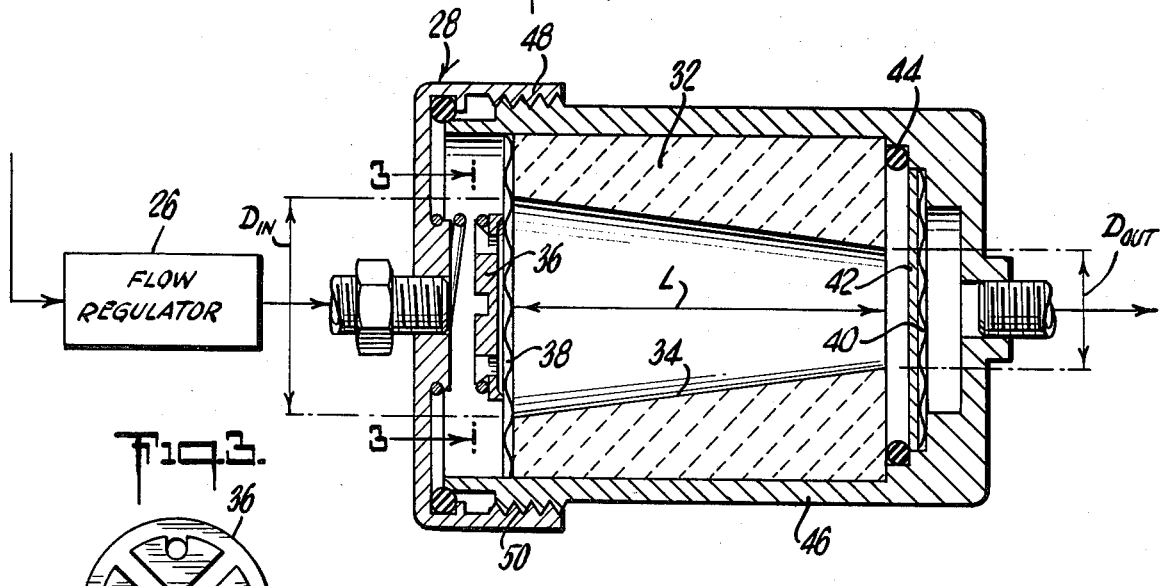

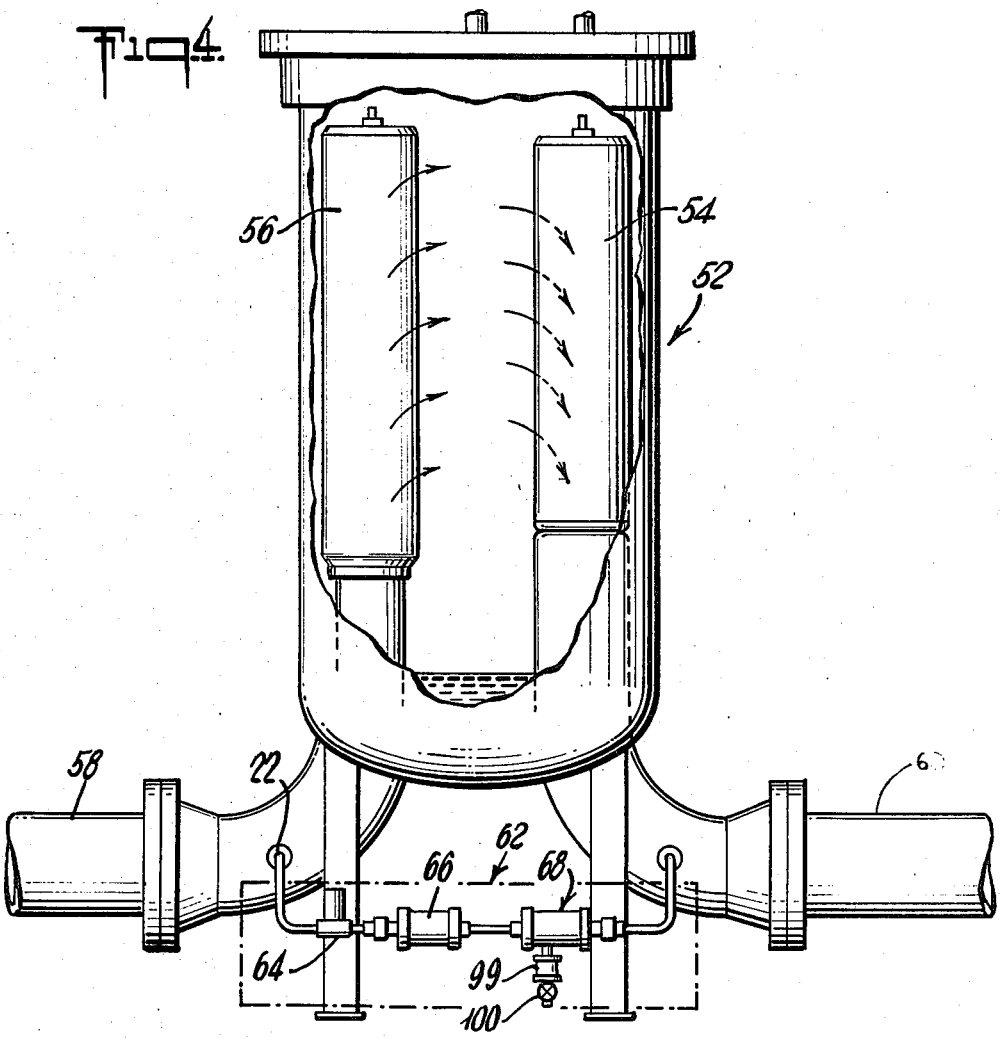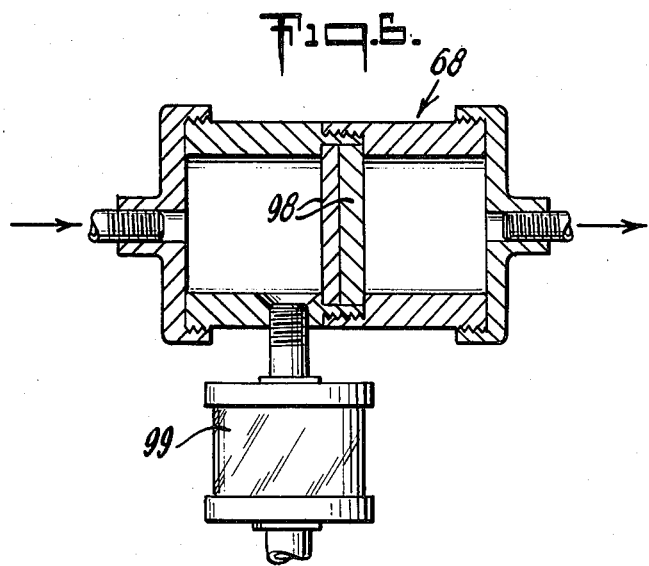

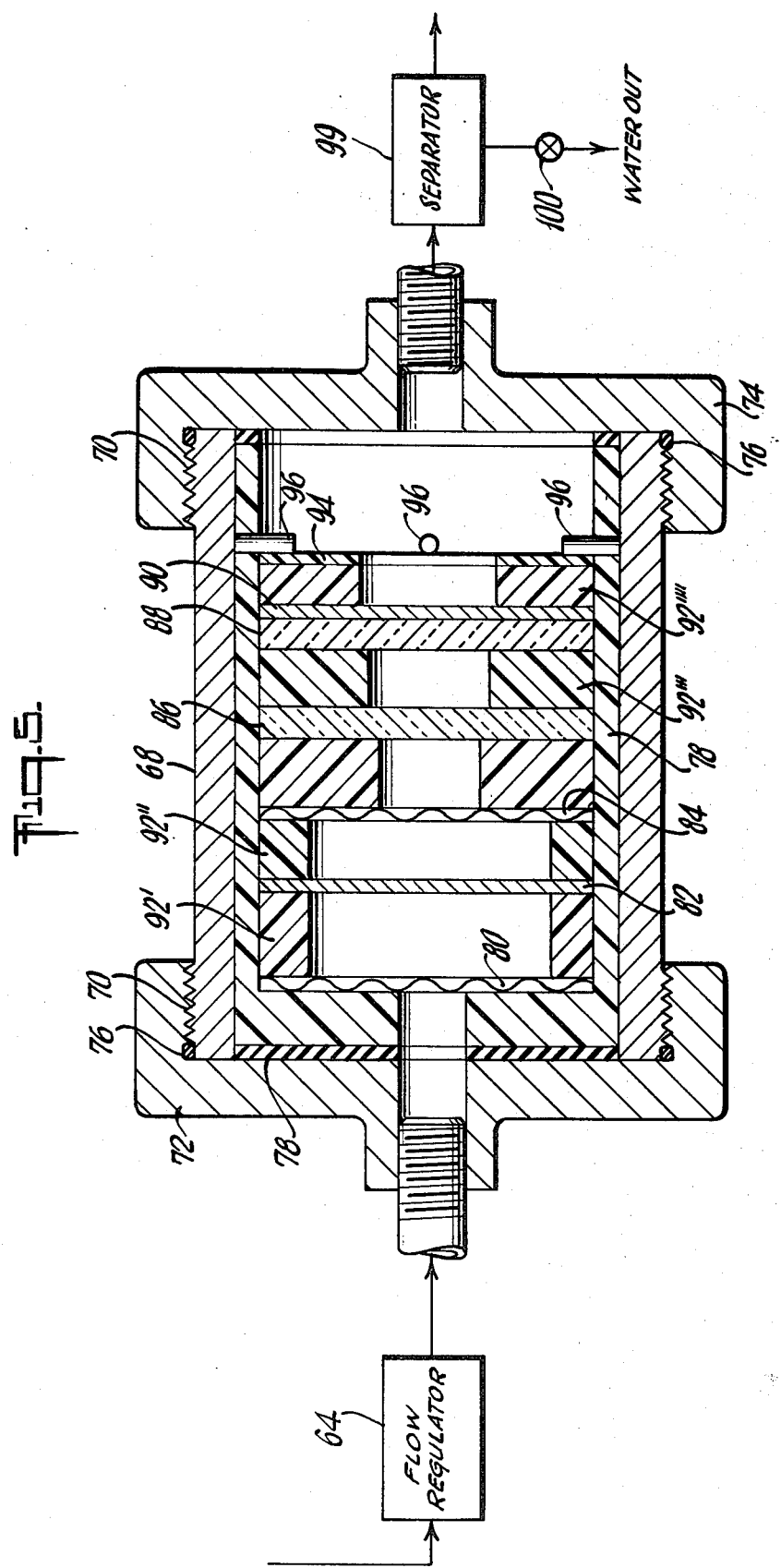

SIDE STREAM MONITORING

This is a continuation of application Ser. No. 58,301, filed July 17, 1979, which is a continuation of appl. Ser. No. 818,154 filed July 22, 1977, both abandoned.

BACKGROUND OF THE INVENTION

Generally, clay filtration is used for the removal of organic contaminants, e.g. surface active agents, which occur naturally in or are added by cross contamination with other petroleum products containing additives. The purpose of removing these surfactants is to improve the water shedding ability of, for example, a liquid fuel and to prevent those surfactants from disarming or deactivating a filter separator which would prevent its use as a filter and as a coalescer and separator of water from the fuel. Clay also is typically used for the removal of organic color bodies from the fuel. Generally, the industry has used attapulgustype clay contained in a bag or canister element in field filtering installations for turbo fuel.

A problem which has heretofore been of substantial concern in connection with clay filtration is the desire and need to measure the ongoing performance of the clay filter in the main unit and its remaining service life. When a high quality fuel is employed, fuel exiting from the filter is of a high quality and nothing is revealed as to the effectiveness of the clay as a filter. However, if a low quality fuel typically containing high surfactant levels is employed, the exiting fuel can be properly analyzed with suitable conventional instrumentation (e.g., a water separometer or a Mini-Sonic Separometer) which will assess the water shedding ability of the fuel, i.e. the ability of the water to be coalesced from the fuel. If the performance of the clay filter to remove the surfactants is poor or ineffective, then the operation must be halted and new clay filter elements installed. Prior to this invention there has been no way to predetermine the remaining clay activity before the low quality fuel is pumped through that filter.

As aviation gas turbine engines have developed there has been an increasing demand for high performance fuel, wherein the degrading effect of a small quantity of contamination will have a severe effect on fuel effectiveness. Conventional control techniques have employed a filter separator which is designed to remove entrained water and solid contaminants from the fuel. These filter separators perform their separation function (i.e., water and solids removal from the hydrocarbon fuel) by providing specific filter media for filtering solids, coalescing medium for coalescing water droplets, and a porous membrane which separates the coalesced water in the fuel. It is necessary for the coalescence to take place prior to any separation.

If the filter separator permits more than a specified amount of solids or water to pass through it to the effluent, then it has failed. Different types or modes of failure can be "mechanical" or what is commonly known as "deactivation". A mechanical failure can be attributed to improper element installation, a pinhole in a new element, or rupture of the filter separator during use. As for deactivation, this can occur even when the filter separator is mechanically sound. Present techniques do not provide for ready detection or prevention of filter deactivation which can affect either the filter coalescer cartridge or separator element without any apparent cause, indication or warning. If deactivation of either element occurs, this will allow contaminants to be passed into the aircraft with the fuel.

DESCRIPTION OF THE PRIOR ART

As mentioned above, heretofore there have been no successful or known devices or methods which will quantatively and readily measure the filter and/or filter separator performance in the field and also predict its remaining service life, at least when either of these elements or components is approaching an inoperable or ineffective stage. It is generally known and common to continuously analyze a flowing stream by establishing a sample loop including an analyzer for certain characteristics of the stream, such as disclosed in U.S. Pat. No. 3,765,226. This expedient, however, is not concerned with the use of a side stream monitoring device or unit having certain critical parameters which duplicate as close as possible a representative segment of the main unit being monitored, such that at any instant without disturbing operation of the main unit, the side monitoring unit can be tested or examined by removal or other suitable means, to provide a ready indication of the performance characteristics of the main unit and also the life expectancy of such segments within the main unit.

Other prior art U.S. patents located during the course of a preliminary investigation for this invention are as follows: Nos.

626,760—Kohn
1,104,203—Dahl
1,187,046—Lamarter
1,515,080—Strachan et al
1,696,735—Scovill
1,943,811—Child et al
2,168,125—Hearn
2,302,552—Johnson
2,679,320—Walton
2,843,077—Leifer
3,077,989—Larkin
3,412,786—Taylor
3,572,507—Juskuvic None of the aforementioned prior art are considered to disclose the above-discussed expedient, which is considered to provide patentability for the present invention. Of these patents, all with the possible exception of Leifer and Taylor relate to full flow filtration designs, while the latter two pertain to pressure sensing devices to indicate fouling by particulates on filters or heat exchange surfaces.

On the other hand, the present invention relates to side stream modeling, both on a physical and dynamic basis, of a main stream filtration unit where removal of the side stream unit and testing under controlled test conditions provides a ready means and indication of assessing the present condition of the main filter, as well as predicting its remaining useful life.

SUMMARY OF THE INVENTION

The present invention relates to side sample stream monitoring of a main unit, which effectively geometrically and dynamically duplicates or simulates operating parameters of the internal operating components in the main unit, which enables the side stream monitoring unit to provide a ready indication and continuous monitor of the performance characteristics and quality of the main unit corresponding features upon removal and testing or examination of the side monitor. The apparatus and method for monitoring have particular utility in connection with clay filters and/or filter separators which are used for the removal of contaminants from liquids such as jet fuels. In each case the bypass side stream is disposed between the inlet and outlet lines of the filter or filter separator and located within the bypass is a unit which effectively is a reduced scale replica of a portion of the main unit which corresponds to the critical operating components thereof. For the clay filters a duplication of flow velocities and residence times of the fuel through a predetermined section of one of the main filter elements is provided. In the case of the filter separator, the side stream unit comprises sections which are comprised of identical components of the elements used in the main unit, including metal screens, fiber sheets, fiberglass screens, etc., except that each component of the side stream monitoring unit has a reduced size such that the ratio of the cross-sectional area to the liquid flow is the same as that which exists in the main filter separator unit for that particular component. Thus, it is seen that the present invention provides a side stream monitoring unit which provides geometrical and dynamic characteristics similar to those of the main unit.

In the case of measuring and monitoring performance of the clay filter independent of the quality of fuel which flows in the main filtration unit, the clay holder located in the side stream between the inlet and outlet lines of the field clay filtration unit, basically duplicates the flow velocities and residence time of the fuel through a small section of one of the main filter elements. To measure the clay performance, the side stream holder containing the same clay as installed in the main unit is removed from the side stream and placed in a small measuring instrument in which various tests are conducted to provide a suitable indication and measure of the clay effectiveness in reference to a known standard. The clay in the holder is renewed each time the elements in the main filter are changed. Flow is proportional through the side stream at all times flow occurs by the main unit which provides a cumulative history of the main filter unit clay.

In the case of the filter separator, the side stream monitoring unit contains the section of actual elements in reduced proportion to those installed in the main filtration unit, to provide a flow rate capacity the same as that in the main unit and also to have a cross-sectional area/flow ratio corresponding to that of the full-sized filter section. This monitor unit can be tested with appropriate instrumentation to provide an indication as to its present state and remaining life. Again, the monitor unit components are changed only when the main unit elements are changed to thereby provide a duplicated and simulated exposure history of the life of the main elements.

BRIEF DESCRIPTION OF THE DRAWINGS

FIG. 1 illustrates a liquid filtration unit having a side stream monitor in accordance with the present invention.

FIG. 2 is an enlarged cross-sectional view of the side stream clay filter holder of FIG. 1.

FIG. 3 is a cross-sectional view taken substantially on the line 3—3 of FIG. 2.

FIG. 4 is a filter separator having a side stream monitor in accordance with the present invention.

FIG. 5 is an enlarged cross-sectional view of the side stream monitor holder for the filter separator of FIG. 4.

FIG. 6 is an enlarged view of the side stream filter holder of FIG. 4.

DESCRIPTION OF THE PREFERRED EMBODIMENTS

FIG. 1 illustrates the side stream monitor according to the present invention in combination with a conventional liquid filter 10, which is designed to remove contaminants from flowing liquid product streams. The filter has an inlet 12 and an outlet 14 with contaminated product entering the inlet and relatively clean product exiting from the outlet. The main filter unit 10 includes a number of cartridges 16, each of which basically comprises a standard filter element which is made of attapulgite and montmorillonite-type clays and are contained either in a woven bag or a canister. These standard filter elements are available from the several commercial suppliers (e.g. Facet Enterprises, Velcon Filters, etc.) and are commonly referred to as clay filter elements. The cartridges are conventionally mounted on a cartridge-mounting plate 18. The flow path of the inlet stream is shown in FIG. 1 by the arrows. A side stream monitor unit generally designated 20 is connected between the inlet and outlet lines 12, 14 respectively. The unit basically may comprise a prefabricated unit which is connected to a conventional ASTM sampling probes 22, 24 at the inlet and at the outlet. The unit includes a rotometer 26 connected in series with a monitor holder 28, which is connected in the side stream line by means of the standard couplings 30 located on either side thereof. The rotometer comprises a standard valve flow regulator. The holder 28, best shown in FIG. 2, is designed to substantially duplicate flow velocities and residence time of the flowing stream, i.e. fuel, which passes through a small section of one of the main filter elements 16 in the main filter unit 10. The holder includes an insert 32 which is generally annular and includes an inner flow passageway 34 of predetermined length L and tapered inwardly in the direction of flow (a truncated conical configuration in cross-section) so as to have a maximum internal inlet diameter $D_{in}$ and a minimum internal outlet diameter $D_{out}$. The clay filter within the holder 28 actually duplicates the main unit clay filter in the amount of clay surface area contacted by the flowing side stream in a predetermined ratio relative to the same parameters in the main unit. At the inlet to the clay filter 32 may be a flow deflector 36 which functions to prevent impingement of the inlet stream on the clay and channelling through the clay and directly adjacent the inlet on the downstream side is a standard wire mesh screen 38 with a similar screen 40 slightly smaller than that at the inlet being disposed at the outlet end. At the outlet a layer of filter paper 42 (also used in the main unit) is located adjacent the screen 40 (on the upstream side), adjacent an O-ring seal 44. The clay used in the side stream monitor is the same as the clay actually installed and employed in the larger monitored vessel and is renewed or changed when the main elements are changed.

Typical dimensions for the side stream monitor unit and in particular the clay filter holder for a 100 ml per minute flow capacity through the side stream unit would be as follows: The $D_{in}=1\frac{1}{2}$ inches, $D_{out}=\frac{3}{4}$ inches, and the $L=2\frac{3}{8}$ inches. These reduced dimensions can be determined by calculating the total flow per unit area of the outer and inner diameters of commercial clay filter elements while operating at rated flow capacity. Rated flow capacity of the elements is specified by the element manufacturer. Unit area is calculated by multiplying the outer or inner element or circumference by the element length. The sidestream monitor diameters are then ratioed to this flow per unit area. It should be understood they are only illustrative and the actual dimensions will depend on actual dimensions of the commercial elements their rated flow capacity and the desired flow rate of the sidestream monitor under these conditions.

When it is desired to measure the performance of the clay in the main unit vis-a-vis analyzing and taking certain predetermined measurements of the clay filter in the side stream monitor, the monitor 78 containing the clay is removed from the side stream and placed in a small portable pump unit which includes a reservoir of predetermined and rated fuel. At that time the flow regulator 30 is closed such that no sample flows through the side stream line. This small pump unit has its own reservoir of reference fuel which may, for example, have a 60–70 MSS rating (this is a conventional rating given fuels as determined by ASTM D-2550 "Test for Water Separation Characteristics of Aviation Turbine Fuels", and contain known quantities of surfactants. The pump forces the fuel at a rated flow capacity (i.e., the same flow per unit area as the main element) through the clay filter monitor holder. A suitable sample (e.g., 50 ml) of effluent fuel is collected and then evaluated for its water shedding ability in conventional instrumentation such as a Mini-sonic Separometer, (manufactured by EMCEE Electronics, Inc., P.O. Box 32, New Castle, Del. 19720), typically that disclosed in U.S. Pat. No. 3,478,578. If a high MSS rating results, which is a reading above 90, that is indicative of satisfactory clay filter performance. However, if the MSS results are between 80 and 90, this is indicative of reduced clay effectiveness, while below a MSS rating of 80 the clay filter is considered ineffective. These tests can be conducted at the filter site since the unit and the pump are portable. Depending on the particular rating obtained from the monitor clay filter, the clay in the main unit can be changed accordingly. By periodic testing of the clay filter in the monitor, a plot of clay effectiveness can be made and at the point where there is a significant deviation, i.e., clay deactivation, then the time for change in the main element is indicated.

It is known that the effectiveness of the clay filter to absorb and remove surfactants from fuel is a function of the residence time or relative fuel velocity, i.e. the time the surfactant laden fuel contacts the clay. This relationship and the results obtained from the testing of the clay monitor in taking effluent samples can provide a means of predicting remaining clay filter service life. Typically, by forcing the fuel through the monitor clay filter at rates higher than its normal rated capacity (i.e., 200% of rated flow capacity per unit area calculated from the flow capacity of the main element), the higher flow rates will result in a lower MSS value before similar value is taken at a rated flow capacity of the filter. This provides an indication of impending clay deactivation and an estimate of remaining clay life. However, since lower than rated flow through the clay improves the clay effectiveness in surfactant removal, analysis of the MSS results obtained from using the clay holder at lower flows can provide a method of predetermining the required reduction in optimum flow rate operation of the main filter unit for maintaining high quality effluent fuels.

Basically what the clay filter in the monitor holder does is to provide the same clay material and to match the flow velocity and the area and volume of the clay filter in a predetermined ratio relative to the main unit filter. Thus, there is provided similarity of geometrical and dynamic or operational characteristics with those of the filter elements in the main unit.

While not shown, the end covers of the holder 28 can be connected through some appropriate means as shown at 46 such as welding to the main body of the holder. To facilitate insertion into and removal of the clay filter from the monitor, the inlet end ($D_{in}$) can have an end cover such as 48 which is threaded as shown at 50 onto the main body or is held in place by means of a quick release coupling of the conventional type (not shown).

Turning now to the embodiment of FIGS. 4 through 6, there is shown a conventional filter separator main unit 52, including a coalescer unit 56 and a separator element 54. Flow is received by the coalescer via the inlet 58. The coalescer is designed to remove solid contaminants, to break the emulsion of the water in a product stream flowing into droplets, and to enlarge the droplets so that they will drop out of the product by gravity. Flow is typically from the inside to the outside of the coalescer. The flow exiting the coalescer and containing the coalesced water droplets then is passed onto the separator element 54 which repels coalesced water droplets and prevents them from going downstream. In the case of the separator, flow is from the outside to the inside as shown by the arrows. The coalesced and separated water collects in a sump for subsequent draw off. Connected between the inlet and outlet of the filter separator (in the same way as the embodiment of FIGS. 1–3) is a side stream monitoring unit 62, the basic device being enclosed in dotted lines. The side stream monitoring unit 62 includes a connection at one end to the standard probe 22 and is coupled also in a conventional manner to the outlet end at 24. The monitor unit includes a section of the actual elements which are installed and in use in the larger vessel being monitored, and are sized to have a flow rated capacity which is compatible and within the capability of an analysis instrument such as the Mini-sonic Separometer. A critical feature is that each of the components of the section filter substantially maintain the same cross sectional area/flow ratio as the full size filter. The monitor elements are changed only when the main unit elements are changed and this provides a duplicated and simulated exposure history of the life of the main elements, as with the prior embodiment. Thus, tests on the filter separator performance can be conducted on the monitor without any disruption of the main unit and can in fact be conducted at any time whether the main unit is in service or not. The present practice to determine the performance of the main elements is to remove the main unit from service, open the vessel and remove a representative element and test in a single element test rig usually located at a remote site. During this period the main unit remains out of service. With the sidestream monitor device this is not the case since testing is conducted on site and requires only ~5 minutes without disruption to the main unit operation.

The side stream monitoring comprises a standard flow regulator 64 (identical to 26) connected in series with a coalescer 66 which duplicates in a same ratio the coalescer and the main unit and optionally can also include a series connected separator 68. The separator side stream monitor 68 is optional since experience has shown that the coalescer deactivates before the separator element. Thus, monitoring of the coalescer is of primary importance. Turning to FIG. 5, there is shown an enlarged illustration and cross-section of the coalescer monitor holder for the side stream. This holder 66 includes an outer housing 68 threaded at opposite ends shown at 70 for receiving an inlet end cap 72 and an outlet end cap 74, each of which may be threaded or one may be secured by other conventional means such as a quick relief coupling while the other end can be welded. Each end cover includes a suitable O-ring seal 76 for preventing leakage of any of the fuel as it passes through the mini-monitor holder. Also at the inlet end can be provided an appropriate gasket 78 for holding the cartridge firmly in place and preventing bypass of any flowing fuel between the filter components and the monitor housing. Within the monitor housing 78 along the axial length thereof are a plurality of spaced filter components which correspond to those in the flow path that the fuel would take in the main unit. These include as an example of a particular commercial filter in the direction of flow perforated screen 80, a pleated paper 82, a second perforated screen 84, fiberglass mats 86 and 88, and a cotton sock 90 which is the outer component of the main filter element. Between the various elements are spacer elements 92, each of which are of a different diameter and are based on calculations of flow per unit area of the main filter unit. The diameter of each of the compartments which would correspond to the flow area and contact surface can be calculated from the main element by calculating the flow per unit area of each component of the filter media of the main element. The unit area is the circumference of the media component multiplied by the element length. The flow per unit area is calculated by dividing the rated flow capacity of the element (as specified by the manufacturer) by the total media component area. The spacer diameter dimensions are then ratioed to the flow per unit area.

FIG. 6 illustrates a monitor holder for the optional separator unit 68 and can include basically the same general construction as the coalescer holder except that the only components therein would be those that would correspond to the actual material employed in the separator installed in the main unit. The component 98 is disposed transverse of the flow and comprises the components of the separator media, which is a replica of separator 54. The device 99 is a water sump where coalesced and separated water collects and can be drained from time to time through valve 100.

In order to test for performance of the filter separator, it is accomplished in generally the same manner as for the embodiment of FIGS. 1-3. Each of the holders containing the element tests sections can be removed from the side stream and placed in Mini-sonic Separometer apparatus and established quantities of reference fluids, for example, 100 MSS fuel and water can be pumped through the holder by the MSS instrument. An effluent sample is taken and measured by a conventional turbidimeter which is included in the MSS apparatus for any uncoalesced water issuing from the filter separator section and uncoalesced water passing through the filter separator reduces light transmission and given a corresponding MSS rating. From this one can determine when deactivation has occurred, if the effluent from the sample filter at the filter flow capacity reaches a predetermined MSS level, e.g. 85. To predict impending deactivation, this can be done by relying on the relationship between the flow rate and the MSS rating of used element sections. As the onset of deactivation approaches, coalescence will become more critical with flow rate and therefore, increased passage of uncoalesced water will occur first at higher than the rated flow of the sectioned coalescer and thereby give a pre-warning of loss of coalescer effectiveness at lower flow rates.

In addition, the filter separator sections which are contained in the side stream monitor also can provide means for monitoring static electricity generated by the different fuels flowing through a particular filter which is used. This can be accomplished by first electrically isolating the filter separator test section and then measuring the flow of current to ground through an electrometer.

Further, while the side stream monitor unit and method has been disclosed for clay filters and filter separators, it also has utility for other units where similar side stream monitoring is desirable or preferred for obtaining a ready indication of performance of the main unit components. This may include such devices as catalyst reactors, where a side stream monitor may be used to measure remaining catalyst activity or catalyst "poisoning". While specific embodiments of the invention and certain modifications thereto have been shown and described in detail to illustrate the application of the inventive principles, it will be understood that the invention may be embodied otherwise without departing from such principles. Various modifications to the inventions will be apparent to those skilled in the art without departing from the scope of the invention to which reference is made in the claims.

What is claimed is:
1. A method of monitoring the performance of a clay filter in a main unit having an inlet and outlet for the passage of a main hydrocarbon fuel stream therethrough, comprising the steps of:
 (a) providing a bypass line externally of said main unit between said inlet and said outlet;
 (b) duplicating in said bypass line geometrical and dynamic characteristics of said clay filter of said main unit by including in said bypass line a monitor device including reduced scale replica of said clay filter of said main unit which has at least proportionate flow velocity and residence time of said main stream through a predetermined section of said clay filter in main unit;
 (c) passing substantially continuously a predetermined sample portion of said main hydrocarbon fuel stream through the replica clay filter in said monitor device when said main hydrocarbon fuel stream passes through said main unit;
 (d) removing said monitor device from said bypass line without disturbing operation of said main unit and passing a reference fuel containing a known amount of surfactant through said monitor device at a flow rate which is greater than the normal rated flow capacity of said clay filter; and
 (e) collecting a sample amount of reference fuel which passes through said monitor device and measuring the water shedding ability of said reference fuel to determine the effectiveness of said monitor clay filter which is an indication of the continued effectiveness of the main stream clay filter.

2. A method of monitoring the performance of filter components in a main filter separator unit having an inlet and outlet for the passage of a main hydrocarbon fuel stream therethrough, comprising the steps of:
  (a) providing a bypass line externally of said main filter separator unit between the said inlet and outlet;
  (b) duplicating in said bypass line geometrical and dynamic characteristics of said filter components of said main unit by including in said bypass line a monitor device including reduced scale replica of said filter components of said main unit to substantially duplicate in said monitor device the ratio of cross-sectional area to liquid flow for at least a predetermined section of said main unit;
  (c) passing substantially continuously a predetermined sample portion of said main hydrocarbon fuel stream through said filter components in said monitor device when said main hydrocarbon fuel stream passes through said main unit;
  (d) removing said monitor device from said bypass line without disturbing operation of said main unit and passing a reference fuel containing a known amount of water through said monitor device at a flow rate which is greater than the normal rated flow rate of said filter separator; and
  (e) collecting a sample amount of reference fuel which passes through said monitor device and measuring the turbidity of said reference fuel to determine the effectiveness of said monitor filter separator which is an indication of the continued effectiveness of the main filter separator.

* * * * *